US008101641B2

(12) United States Patent
Almstead et al.

(10) Patent No.: US 8,101,641 B2
(45) Date of Patent: Jan. 24, 2012

(54) HYDROXYLATED 1,2,4-OXADIAZOLE BENZOIC ACID COMPOUNDS AND COMPOSITIONS THEREOF

(75) Inventors: Neil G. Almstead, Princeton, NJ (US); Peter Seongwoo Hwang, Edison, NJ (US); Young-Choon Moon, Belle Mead, NJ (US); Ellen M. Welch, Califon, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 11/904,001

(22) Filed: Sep. 24, 2007

(65) Prior Publication Data

US 2008/0139632 A1  Jun. 12, 2008

Related U.S. Application Data

(60) Provisional application No. 60/847,327, filed on Sep. 25, 2006.

(51) Int. Cl.
*A61K 31/4245* (2006.01)
*C07D 271/06* (2006.01)

(52) U.S. Cl. .................. 514/364; 548/131
(58) Field of Classification Search .......... 514/364; 548/131
See application file for complete search history.

(56) References Cited

U.S. PATENT DOCUMENTS

| | | | |
|---|---|---|---|
| 6,660,753 | B2 | 12/2003 | Van Wagenen et al. |
| 6,759,538 | B2 | 7/2004 | Singh et al. |
| 6,992,096 | B2 * | 1/2006 | Karp et al. ............ 514/364 |
| 7,041,685 | B2 | 5/2006 | Cai et al. |
| 7,112,595 | B2 | 9/2006 | Wagenen et al. |
| 7,153,880 | B2 | 12/2006 | Singh et al. |
| 7,202,262 | B2 | 4/2007 | Karp et al. |
| 2004/0132726 | A1 | 7/2004 | Arora et al. |
| 2004/0204461 | A1 * | 10/2004 | Karp et al. ............ 514/364 |
| 2005/0075375 | A1 | 4/2005 | Vourloumis et al. |
| 2005/0164973 | A1 | 7/2005 | Karp et al. |
| 2006/0089365 | A1 | 4/2006 | Hintermann et al. |
| 2006/0148863 | A1 | 7/2006 | Karp et al. |
| 2006/0148864 | A1 | 7/2006 | Karp et al. |
| 2007/0161687 | A1 | 7/2007 | Karp et al. |

FOREIGN PATENT DOCUMENTS

| | | |
|---|---|---|
| WO | WO 97/41105 | 11/1997 |
| WO | WO 99/21852 | 5/1999 |
| WO | WO 2006/110483 | 10/2006 |
| WO | WO 2006/121390 | 11/2006 |
| WO | WO 2006121390 A2 * | 11/2006 |

OTHER PUBLICATIONS

Welch et al., 2007, "PTC124 Targets Genetic Disorders Caused by Nonsense Mutations," *Nature* 447:87-91.
Supplementary Information from Welch et al., 2007, "PTC124 Targets Genetic Disorders Caused by Nonsense Mutations," *Nature* 447:87-91 (pp. 1-23).
Hirawat et al., 2007, "Safety, Tolerability, and Pharmacokinetics of PTC124, a Nonaminoglycoside Nonsense Mutation Suppressor, Following Single- and Multiple-Dose Administration to Healthy Male and Female Adult Volunteers," *Journal of Clinical Pharmacology* 47(4):430-444.
Du et al., 2008, "PTC124 is an orally bioavailable compound that promotes suppression of the human CFTR-G542X nonsense allele in a CF mouse model." *PNAS* 105(6):2064-2069.
Kerem et al., 2008, "Effectiveness of PTC124 treatment of cystic fibrosis caused by nonsense mutations: a prospective phase II trial," *The Lancet* 372:719-27.
Auld et al., 2009, "Mechanism of PTC124 activity in cell based luciferase assays of nonsense codon suppression," *PNAS Early Edition*:1-6 (document sent via fax Jan. 28, 2009).
Auld et al., 2009, "Mechanism of PTC124 activity in cell based luciferase assays of nonsense codon suppression," *PNAS Early Edition*:1-6 (document previously available from www.genome.gov website in Feb. 2008).
Auld et al., 2009, "Mechanism of PTC124 activity in cell based luciferase assays of nonsense codon suppression," *PNAS Early Edition*:1-6.
Supplemental Information Methods from Auld et al., 2009, "Mechanism of PTC124 activity in cell based luciferase assays of nonsense codon suppression," *PNAS Early Edition*:1-6 (pp. 1-17).
Knapman, 2000, "Polymorphic predictions—Understanding the nature of crystalline compounds can be critical in drug development and manufacture," *Modern Drug Discovery*, Mar. 2000, pp. 53-57.
U.S. Appl. No. 11/899,813, filed Sep. 6, 2007, Almstead et al.
U.S. Appl. No. 60/269,847, filed Feb. 21, 2001, Van Wagenen et al.
U.S. Appl. No. 60/149,464, filed Aug. 19, 1999, Van Wagenen et al.
U.S. Appl. No. 60/405,472, filed Aug. 23, 2002, Singh et al.
U.S. Appl. No. 60/350,107, filed Nov. 2, 2001, Singh et al.

* cited by examiner

*Primary Examiner* — Yong Chu
(74) *Attorney, Agent, or Firm* — Jones Day

(57) ABSTRACT

Novel hydroxylated 1,2,4-oxadiazole benzoic acid compounds, methods of using and pharmaceutical compositions comprising a hydroxylated 1,2,4-oxadiazole benzoic acid derivative are disclosed. The methods include methods of treating or preventing a disease ameliorated by modulation of premature translation termination or nonsense-mediated mRNA decay, or ameliorating one or more symptoms associated therewith.

8 Claims, No Drawings

HYDROXYLATED 1,2,4-OXADIAZOLE BENZOIC ACID COMPOUNDS AND COMPOSITIONS THEREOF

This application claims the benefit of U.S. provisional application No. 60/847,327, filed Sep. 25, 2006, which is incorporated by reference herein in its entirety.

1. FIELD OF INVENTION

The invention relates to hydroxyl substituted 1,2,4-oxadiazole benzoic acid compounds, compositions comprising the compounds and methods for treating or preventing diseases associated with nonsense mutations of mRNA by administering these compounds or compositions.

2. BACKGROUND OF THE INVENTION

Gene expression in cells depends upon the sequential processes of transcription and translation. Together, these processes produce a protein from the nucleotide sequence of its corresponding gene.

Insertions, deletions, transition and transversion mutations of a DNA sequence can all result in a nonsense mutation, or chain termination mutation, in which the base mutation or frameshift mutation changes an amino acid codon into one of the three stop codons. These premature stop codons can produce aberrant proteins in cells as a result of premature translation termination. A nonsense mutation in an essential gene can be lethal and can also result in a number of diseases, such as, cancers, lysosomal storage disorders, the muscular dystrophies, cystic fibrosis and hemophilia, to name a few.

Small molecule therapeutics or prophylactics that suppress premature translation termination by mediating the misreading of the nonsense codon would be useful for the treatment of a number of diseases. The discovery of small molecule drugs, particularly orally bioavailable drugs, may lead to the introduction of a broad spectrum of selective therapeutics which can be used against disease caused by nonsense mutations.

3. SUMMARY OF THE INVENTION

The invention relates to compounds of formula I:

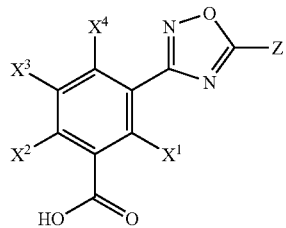

(I)

or pharmaceutically acceptable salts, hydrates, clathrates, prodrugs, polymorphs, stereoisomers, including enantiomers, diastereomers, racemates or mixtures of stereoisomers, thereof wherein:

Z is substituted or unsubstituted aryl, substituted or unsubstituted heteroaryl, substituted or unsubstituted cycloalkyl, substituted or unsubstituted alkyl, substituted or unsubstitued alkenyl, substituted or unsubstituted heterocycle, substituted substituted arylalkyl, or aryloxyalkyl; and $X^1$, $X^2$, $X^3$ and $X^4$ are independently H or OH, and at least one of $X^1$, $X^2$, $X^3$ or $X^4$ is OH.

In a particular embodiment, Z is substituted aryl.
In another embodiment, Z is halo substituted aryl.
In another embodiment, Z is fluoro substituted aryl.
In another embodiment, Z is substituted phenyl.
In another embodiment, Z is halo substituted phenyl.
In another embodiment, Z is fluoro substituted phenyl.
In one embodiment, this invention encompasses compounds of formula II:

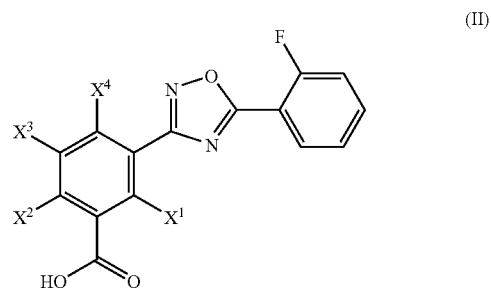

(II)

wherein:
$X^1$, $X^2$, $X^3$ and $X^4$ are as described herein.

Further embodiments of the invention include, but are not limited to:
3-[5-(2-fluorophenyl)-[1,2,4]oxadiazol-3-yl]-2-hydroxybenzoic acid;
5-[5-(2-fluorophenyl)-[1,2,4]oxadiazol-3-yl]-2-hydroxybenzoic acid;
3-[5-(2-fluorophenyl)-[1,2,4]oxadiazol-3-yl]-5-hydroxybenzoic acid;
3-[5-(2-fluorophenyl)-[1,2,4]oxadiazol-3-yl]-4-hydroxybenzoic acid;
3-[5-(2-fluorophenyl)-[1,2,4]oxadiazol-3-yl]-2,6-dihydroxybenzoic acid;
3-[5-(2-fluorophenyl)-[1,2,4]oxadiazol-3-yl]-2,5-dihydroxybenzoic acid;
3-[5-(2-fluorophenyl)-[1,2,4]oxadiazol-3-yl]-2,4-dihydroxybenzoic acid;
5-[5-(2-fluorophenyl)-[1,2,4-oxadiazol-3-yl]-2,3-dihydroxybenzoic acid;
5-[5-(2-fluorophenyl)-[1,2,4]oxadiazol-3-yl]-2,4-dihydroxybenzoic acid;
3-[5-(2-fluorophenyl)-[1,2,4]oxadiazol-3-yl]-4,5-dihydroxybenzoic acid;
3-[5-(2-fluorophenyl)-[1,2,4]oxadiazol-3-yl]-2,5,6-trihydroxybenzoic acid;
3-[5-(2-fluorophenyl)-[1,2,4]oxadiazol-3-yl]-2,4,6-trihydroxybenzoic acid;
3-[5-(2-fluorophenyl)-[1,2,4]oxadiazol-3-yl]-2,4,5-trihydroxybenzoic acid;
5-[5-(2-fluorophenyl)-[1,2,4]oxadiazol-3-yl]-2,3,4-trihydroxybenzoic acid;
3-[5-(2-fluorophenyl)-[1,2,4]oxadiazol-3-yl]-2,4,5,6-tetrahydroxybenzoic acid;
3-[5-(4-Fluoro-phenyl)-[1,2,4]oxadiazol-3-yl]-4-hydroxybenzoic acid;
3-[5-(3-Fluoro-phenyl)-[1,2,4]oxadiazol-3-yl]-4-hydroxybenzoic acid;
4-Hydroxy-3-(5-m-tolyl-[1,2,4]oxadiazol-3-yl)-benzoic acid;
3-[5-(3-Chloro-phenyl)-[1,2,4]oxadiazol-3-yl]-4-hydroxybenzoic acid;
4-Hydroxy-3-(5-phenyl-[1,2,4]oxadiazol-3-yl)-benzoic acid;

3-[5-(4-Chloro-phenyl)-[1,2,4]oxadiazol-3-yl]-4-hydroxy-benzoic acid;
3-[5-(2-Chloro-phenyl)-[1,2,4]oxadiazol-3-yl]-4-hydroxy-benzoic acid;
4-Hydroxy-3-[5-(2-hydroxy-phenyl)-[1,2,4]oxadiazol-3-yl]-benzoic acid;
3-[5-(3-Bromo-phenyl)-[1,2,4]oxadiazol-3-yl]-4-hydroxy-benzoic acid;
3-[5-(4-tert-Butyl-phenyl)-[1,2,4]oxadiazol-3-yl]-4-hydroxy-benzoic acid;
3-(5-Ethyl-[1,2,4]oxadiazol-3-yl)-4-hydroxy-benzoic acid;
3-[5-(2,4-Difluoro-phenyl)-[1,2,4]oxadiazol-3-yl]-4-hydroxy-benzoic acid;
3-[5-(2,4-Dichloro-5-fluoro-phenyl)-[1,2,4]oxadiazol-3-yl]-4-hydroxy-benzoic acid;
3-[5-(4-Cyano-phenyl)-[1,2,4]oxadiazol-3-yl]-4-hydroxy-benzoic acid;
3-[5-(4-Dimethylamino-phenyl)-[1,2,4]oxadiazol-3-yl]-4-hydroxy-benzoic acid;
3-[5-(5-Bromo-pyridin-3-yl)-[1,2,4]oxadiazol-3-yl]-4-hydroxy-benzoic acid;
3-[5-(2,3-Difluoro-phenyl)-[1,2,4]oxadiazol-3-yl]-4-hydroxy-benzoic acid;
3-[5-(5-Chloro-pyridin-3-yl)-[1,2,4]oxadiazol-3-yl]-4-hydroxy-benzoic acid;
4-Hydroxy-3-[5-(4-hydroxy-phenyl)-[1,2,4]oxadiazol-3-yl]-benzoic acid;
4-Hydroxy-3-(5-phenoxymethyl-[1,2,4]oxadiazol-3-yl)-benzoic acid;
4-Hydroxy-3-[5-(3-trifluoromethyl-phenyl)-[1,2,4]oxadiazol-3-yl]-benzoic acid;
3-[5-(2,5-Difluoro-phenyl)-[1,2,4]oxadiazol-3-yl]-4-hydroxy-benzoic acid;
3-[5-(3,5-Difluoro-phenyl)-[1,2,4]oxadiazol-3-yl]-4-hydroxy-benzoic acid;
3-[5-(3,5-Bis-trifluoromethyl-phenyl)-[1,2,4]oxadiazol-3-yl]-4-hydroxy-benzoic acid;
3-[5-(2-Fluoro-4-trifluoromethyl-phenyl)-[1,2,4]oxadiazol-3-yl]-4-hydroxy-benzoic acid;
3-[5-(2-Fluoro-5-trifluoromethyl-phenyl)-[1,2,4]oxadiazol-3-yl]-4-hydroxy-benzoic acid;
4-Hydroxy-3-[5-(2,4,6-trichloro-phenyl)-[1,2,4]oxadiazol-3-yl]-benzoic acid;
3-[5-(3-Cyano-phenyl)-[1,2,4]oxadiazol-3-yl]-4-hydroxy-benzoic acid;
3-(5-Biphenyl-4-yl-[1,2,4]oxadiazol-3-yl)-4-hydroxy-benzoic acid;
3-[5-(2-Fluoro-3-trifluoromethyl-phenyl)-[1,2,4]oxadiazol-3-yl]-4-hydroxy-benzoic acid;
4-Hydroxy-3-(5-naphthalen-1-yl-[1,2,4]oxadiazol-3-yl)-benzoic acid;
4-Hydroxy-3-[5-(3-nitro-phenyl)-[1,2,4]oxadiazol-3-yl]-benzoic acid;
3-(5-Butyl-[1,2,4]oxadiazol-3-yl)-4-hydroxy-benzoic acid;
4-Hydroxy-3-[5-(2-methoxy-phenyl)-[1,2,4]oxadiazol-3-yl]-benzoic acid;
3-(5-But-2-enyl-[1,2,4]oxadiazol-3-yl)-4-hydroxy-benzoic acid;
4-Hydroxy-3-[5-(4-trifluoromethyl-phenyl)-[1,2,4]oxadiazol-3-yl]-benzoic acid;
4-Hydroxy-3-[5-(3-sulfo-phenyl)-[1,2,4]oxadiazol-3-yl]-benzoic acid;
3-[5-(4-Bromo-phenyl)-[1,2,4]oxadiazol-3-yl]-4-hydroxy-benzoic acid;
3-(5-Benzyl-[1,2,4]oxadiazol-3-yl)-4-hydroxy-benzoic acid;
4-Hydroxy-3-[5-(4-nitro-phenyl)-[1,2,4]oxadiazol-3-yl]-benzoic acid, and
4-Hydroxy-3-(5-isopropyl-[1,2,4]oxadiazol-3-yl)-benzoic acid.

The invention further encompasses methods of treating or preventing a disease ameliorated by modulation of premature translation termination or nonsense-mediated mRNA decay, or ameliorating one or more symptoms associated therewith, comprising administering to a patient in need thereof a therapeutically or prophylactically effective amount of a compound of formula I and II.

The invention further encompasses methods of treating or preventing, or ameliorating a genetic disease, cancer, or one or more symptoms associated with or manifestations of a genetic disease and cancer, comprising administering to a patient in need thereof a therapeutically or prophylactically effective amount of a compound of formula I and II.

Without being limited to any particular theory, the ability of the compounds of formula I and II to promote readthrough of stop codons makes them useful in the treatment or prevention of any disease which is caused in whole or in part by a nonsense mutation. Examples of such diseases are described herein, and are well known to those skilled in the art, such as those skilled in the art of genetic diseases. Such diseases can occur due to the decreased amount of active protein produced as a result of premature termination of translation. Without being limited to any particular theory, the compounds of formula I and II allow the translation of mRNA to continue past the nonsense mutation resulting in the production of full length protein. A powerful aspect of the invention is that the therapeutic activity of compounds of formula I and II are not necessarily disease specific, instead are effective at treating of preventing any disease associated with a nonsense mutation. Further, the methods of the invention may be patient specific. That is, a patient may be screened to determine if this disease is associated with a nonsense mutation. If so, they can be treated with a compound of the invention.

The present invention encompasses the in vitro or in vivo use of a compound of the invention, and the incorporation of a compound of the invention into pharmaceutical compositions and single unit dosage forms useful in the treatment and prevention of a variety of diseases and disorders. Specific diseases and disorders include those ameliorated by the suppression of a nonsense mutation in messenger RNA.

Pharmaceutical compositions including dosage forms of the invention, which comprise a compound of the invention or a pharmaceutically acceptable polymorph, prodrug, salt, clathrate, solvate or hydrate thereof, can be used in the methods of the invention.

3.1 Definitions

As used herein, unless otherwise specified, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include -methyl, -ethyl, -n-propyl, -n-butyl, -n-pentyl, -n-hexyl, -n-heptyl, -n-octyl, -n-nonyl, and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-dimethylpentyl, 3,3-diethylhexyl, 2,2-diethylhexyl, 3,3-diethylhexyl and the like. An alkyl group can be unsubstituted or substituted.

As used herein, unless otherwise specified the term "alkenyl group" means a straight chain or branched non-cyclic hydrocarbon having from 2 to 20 carbon atoms, more preferably 2-10 carbon atoms, most preferably 2-6 carbon atoms, and including at least one carbon-carbon double bond. Representative straight chain and branched ($C_2$-$C_{10}$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. The double bond of an alkenyl group can be unconjugated or conjugated to another unsaturated group. An alkenyl group can be unsubstituted or substituted.

As used herein, unless otherwise specified the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5,6,7,8-tetrahydronaphthyl and the like. Preferably, the aryl group is a monocyclic ring or bicyclic ring. Representative aryl groups include phenyl, tolyl, anthracenyl, fluorenyl, naphthalene, indenyl, azulenyl, phenanthrenyl and naphthyl. A carbocyclic aryl group can be unsubstituted or substituted.

As used herein, unless otherwise specified the term "heteroaryl" means a carbocyclic aromatic ring containing from 5 to 14 ring atoms and the ring atoms contain at least one heteroatom, preferably 1 to 3 heteroatoms, independently selected from nitrogen, oxygen, or sulfur. Heteroaryl ring structures include compounds having one or more ring structures such as mono-, bi-, or tricyclic compounds as well as fused heterocycle moieties. Representative heteroaryls are triazolyl, tetrazolyl, oxadiazolyl, pyridyl, furyl, benzofuranyl, thiophenyl, benzothiophenyl, benzoisoxazolyl, benzoisothiazolyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, acridinyl, pyrimidyl and oxazolyl. A group can be unsubstituted or substituted.

As used herein, unless otherwise specified the term "cycloalkyl" means a monocyclic or polycyclic saturated ring comprising carbon and hydrogen atoms and having no carbon-carbon multiple bonds. A cycloalkyl group can be unsubstituted or substituted. Examples of cycloalkyl groups include, but are not limited to, ($C_3$-$C_7$)cycloalkyl groups, including cyclopropyl, cyclobutyl, cyclopentyl, cyclohexyl, and cycloheptyl, and saturated cyclic and bicyclic terpenes. A cycloalkyl group can be unsubstituted or substituted. Preferably, the cycloalkyl group is a monocyclic ring or bicyclic ring.

As used herein, unless otherwise specified the term "heterocycle" means a monocyclic or polycyclic ring comprising carbon and hydrogen atoms, optionally having 1 to 4 multiple bonds, and the ring atoms contain at least one heteroatom, preferably 1 to 3 heteroatoms, independently selected from nitrogen, oxygen, and sulfur. Heterocyclyl ring structures include compounds having one or more ring structures such as mono-, bi-, or tricyclic compounds. Preferably, the heterocyclyl group is a monocyclic ring or bicyclic ring. Representative heterocycles include, but are not limited to morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, and the like. A heterocyclyl ring can be unsubstituted or substituted.

As used herein, unless otherwise specified the term "arylalkyl" means -(alkyl)-(aryl), wherein alkyl and aryl are defined above, including, but not limited to —($CH_2$)phenyl, —($CH_2$)$_2$-phenyl, —($CH_2$)$_3$-phenyl, —CH(phenyl)$_2$, —CH(phenyl)$_3$, —($CH_2$)tolyl, —($CH_2$)anthracenyl, —($CH_2$)fluorenyl, —($CH_2$)indenyl, —($CH_2$)azulenyl, —($CH_2$)naphthyl, and the like.

The term "aryloxyalkyl," as used herein, refers to an aryl group, as defined herein, appended to the parent molecular moiety through a "—O-alkyl" group, with alkyl as defined herein.

As used herein, unless otherwise specified the term "halogen" or "halo" means fluorine, chlorine, bromine, or iodine.

As used herein, unless otherwise specified, the term "substituted" means a group may be substituted by one or more independent substituents, examples of which include, but are not limited to, halo, alkyl, alkoxy, trifluoromethyl, trifluoromethoxy, hydroxy, alkoxy, cycloalkyoxy, heterocyclooxy, oxo, alkanoyl, alkylcarbonyl, cycloalkyl, aryl, aryloxy, aralkyl, alkanoyloxy, cyano, azido, amino, alkylamino, —S(O)$_2$OH, arylamino, aralkylamino, cycloalkylamino, heterocycloamino, mono and disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, oxygen, sulfonamido (e.g., $SO_2NH_2$), substituted sulfonamido, nitro, carboxy, carbamyl (e.g. $CONH_2$), substituted carbamyl (e.g., CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclo, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl. In a particular embodiment, the term substituted does not mean cyano.

As used herein, "premature translation termination" refers to the result of a mutation that changes a codon corresponding to an amino acid to a stop codon.

As used herein, "nonsense-mediated mRNA decay" refers to any mechanism that mediates the decay of mRNAs containing a premature translation termination codon.

As used herein, a "premature termination codon" or "premature stop codon" refers to the occurrence of a stop codon where a codon corresponding to an amino acid should be.

As used herein, a "nonsense mutation" is a point mutation changing a codon corresponding to an amino acid to a stop codon.

As used herein, "nonsense suppression" refers to the inhibition or suppression of premature translation and/or nonsense-mediated mRNA decay.

As used herein, "modulation of premature translation termination and/or nonsense-mediated mRNA decay" refers to the regulation of gene expression by altering the level of nonsense suppression. For example, if it is desirable to increase production of a defective protein encoded by a gene with a premature stop codon, i.e., to permit readthrough of the premature stop codon of the disease gene so translation of the gene can occur, then modulation of premature translation termination and/or nonsense-mediated mRNA decay entails up-regulation of nonsense suppression. Conversely, if it is desirable to promote the degradation of an mRNA with a premature stop codon, then modulation of premature translation termination and/or nonsense-mediated mRNA decay entails down-regulation of nonsense suppression.

As used herein, the term "patient" means an animal (e.g., cow, horse, sheep, pig, chicken, turkey, quail, cat, dog, mouse, rat, rabbit, guinea pig, etc.), preferably a mammal such as a non-primate and a primate (e.g., monkey and human), most preferably a human. In certain embodiments, the patient is an infant, child, adolescent or adult. In one embodiment, it has been determined through pre-screening that the patient possesses a non-sense mutation. In another embodiment, it has been determined through pre-screening which non-sense mutation the patient has (i.e., UAA, UGA, or UAG). In another embodiment, the patient is infected with bacterial cells (e.g., *Pseudomonas aeruginosa*). In another embodiment, the cells of the patient are virally infected.

As used herein, a "therapeutically effective amount" refers to that amount of the compound of the invention sufficient to provide a therapeutic benefit in the treatment or management of the disease or to delay or minimize symptoms associated with the disease. Further, a therapeutically effective amount with respect to a compound of the invention means that amount of therapeutic agent alone, or in combination with other therapies, that provides a therapeutic benefit in the treatment or management of the disease. Used in connection with an amount of a compound of the invention, the term can encompass an amount that improves overall therapy, reduces or avoids symptoms or causes of disease, or enhances the therapeutic efficacy of or synergies with another therapeutic agent.

As used herein, a "prophylactically effective amount" refers to that amount of a compound of the invention sufficient to result in the prevention, recurrence or spread of the disease. A prophylactically effective amount may refer to the amount sufficient to prevent initial disease or the recurrence or spread of the disease or the occurrence of the disease in a patient, including but not limited to those predisposed to the disease. A prophylactically effective amount may also refer to the amount that provides a prophylactic benefit in the prevention of the disease. Further, a prophylactically effective amount with respect to a compound of the invention means that amount alone, or in combination with other agents, that provides a prophylactic benefit in the prevention of the disease. Used in connection with an amount of a compound of the invention, the term can encompass an amount that improves overall prophylaxis or enhances the prophylactic efficacy of or synergies with another prophylactic agent.

As used herein, a "therapeutic protocol" refers to a regimen of timing and dosing of one or more therapeutic agents.

As used herein, a "prophylactic protocol" refers to a regimen of timing and dosing of one or more prophylactic agents.

A used herein, a "protocol" includes dosing schedules and dosing regimens.

As used herein, "in combination" refers to the use of more than one prophylactic and/or therapeutic agents.

As used herein, the terms "prevent", "preventing" and "prevention" refer to the prevention of the onset recurrence, spread or of the disease in a subject resulting from the administration of a prophylactic or therapeutic agent.

As used herein, the terms "treat", "treating" and "treatment" refer to the eradication or amelioration of the disease or symptoms associated with the disease. In certain embodiments, such terms refer to minimizing the spread or worsening of the disease resulting from the administration of one or more prophylactic or therapeutic agents to a subject with such a disease.

As used herein, the term "pharmaceutically acceptable salts" refer to salts prepared from pharmaceutically acceptable non-toxic acids or bases including inorganic acids and bases and organic acids and bases. Suitable pharmaceutically acceptable base addition salts for the compound of the present invention include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Other examples of salts are well known in the art, see, e.g., *Remington's Pharmaceutical Sciences,* 18th ed., Mack Publishing, Easton Pa. (1995).

As used herein and unless otherwise indicated, the term "optically pure" or "stereomerically pure" means a the stereoisomer of a compound is substantially free of the other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, more preferably greater than about 97% by weight of one stereoisomer of the compound and less than about 3% by weight of the other stereoisomers of the compound, more preferably greater than about 98% by weight of one stereoisomer of the compound and less than about 2% by weight of the other stereoisomers of the compound, more preferably greater than about 99% by weight of one stereoisomer of the compound and less than about 1% by weight of the other stereoisomers of the compound, and more preferably greater than about 99.5% by weight of one stereoisomer of the compound and less than about 0.5% by weight of the other stereoisomers of the compound.

As used herein and unless otherwise indicated, the term "enantiomerically pure" means a stereomerically pure composition of a compound having one chiral center.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4. DETAILED DESCRIPTION OF THE INVENTION

4.1 Biological Assays and Animal Studies

Compounds that modulate premature translation termination and/or nonsense-mediated mRNA decay can be identified by a number of techniques. For example, methods for screening compounds that modulate the post-transcriptional expression of any gene with a premature translation stop codon are described in International Patent Publication No. WO 01/44516 A2, incorporated herein in its entirety by reference. In a preferred embodiment, a mRNA with a premature termination codon is translated in vitro and is used to screen a library of test compounds. In a preferred embodiment, the mRNA with a premature termination codon is a reporter gene with a premature termination codon.

Two assays were developed for use in high throughput screens to identify small molecules that promote nonsense suppression. Each assay utilized luciferase because it is a functional reporter gene assay (light is only produced if the protein is functional) and it is extremely sensitive (Light intensity is proportional to luciferase concentration in the nM range). The first assay is a cell-based luciferase reporter assay and the second is a biochemical assay consisting of rabbit reticulocyte lysate and a nonsense-containing luciferase reporter mRNA. In the cell-based assay, a luciferase reporter construct containing a UGA premature termination codon was stably transfected in 293T Human Embryonic Kidney cells. In the biochemical assay, mRNA containing a UGA premature termination codon was used as a reporter in an in vitro translation reaction using rabbit reticulocyte lysate supplemented with tRNA, hemin, creatine kinase, amino acids, KOAc, Mg(OAc)$_2$, and creatine phosphate. Translation of the mRNA was initiated within a virus derived leader sequence, which significantly reduced the cost of the assay because capped RNA was not required. Synthetic mRNA was prepared in vitro using the T7 promoter and the MegaScript in vitro transcription kit (Ambion). In both of the biochemical and cell-based assays, addition of a small molecule known to allow readthrough of premature termination codons, 3-[3-(4-Isopropyl-phenyl)-2,5-dioxo-imidazolidin-1-yl]-benzoic acid, resulted in increased luciferase activity and was, therefore, used as an internal standard.

Animal model systems can also be used to demonstrate the safety and efficacy of compounds of formula I and II. The compounds of formula I and II can be tested for biological activity using animal models for a disease, condition, or syndrome of interest, as is commonly known to those skilled in the art. These include animals engineered to contain the target RNA element coupled to a functional readout system, such as a transgenic mouse.

Examples of animal models for cystic fibrosis include, but are not limited to, cftr(−/−) mice (see, e.g., Freedman et al., 2001, Gastroenterology 121(4):950-7), cftr(tm1HGU/tm1HGU) mice (see, e.g., Bernhard et al., 2001, Exp Lung Res 27(4):349-66), CFTR-deficient mice with defective cAMP-mediated Cl(−) conductance (see, e.g., Stotland et al., 2000, Pediatr Pulmonol 30(5):413-24), and C57BL/6-Cftr (m1UNC)/Cftr(m1UNC) knockout mice (see, e.g., Stotland et al., 2000, Pediatr Pulmonol 30(5):413-24).

Examples of animal models for muscular dystrophy include, but are not limited to, mouse, hamster, cat, dog, and C. elegans. Examples of mouse models for muscular dystrophy include, but are not limited to, the dy−/− mouse (see, e.g., Connolly et al., 2002, J Neuroimmunol 127(1-2):80-7), a muscular dystrophy with myositis (mdm) mouse mutation (see, e.g., Garvey et al., 2002, Genomics 79(2):146-9), the mdx mouse (see, e.g., Nakamura et al., 2001, Neuromuscul Disord 11 (3):251-9), the utrophin-dystrophin knockout (dko) mouse (see, e.g., Nakamura et al., 2001, Neuromuscul Disord 11(3):251-9), the dy/dy mouse (see, e.g., Dubowitz et al., 2000, Neuromuscul Disord 10(4-5):292-8), the mdx (Cv3) mouse model (see, e.g., Pillers et al., 1999, Laryngoscope 109(8): 1310-2), and the myotonic ADR-MDX mutant mice (see, e.g., Kramer et al., 1998, Neuromuscul Disord 8(8):542-50).

Examples of animal models for familial hypercholesterolemia include, but are not limited to, mice lacking functional LDL receptor genes (see, e.g., Aji et al., 1997, Circulation 95(2):430-7), Yoshida rats (see, e.g., Fantappie et al., 1992, Life Sci 50(24):1913-24), the JCR:LA-cp rat (see, e.g., Richardson et al., 1998, Atherosclerosis 138(1):135-46), swine (see, e.g., Hasler-Rapacz et al., 1998, Am J Med Genet. 76(5): 379-86), and the Watanabe heritable hyperlipidaemic rabbit (see, e.g., Tsutsumi et al., 2000, Arzneimittelforschung 50(2): 118-21; Harsch et al., 1998, Br J Pharmacol 124(2):227-82; and Tanaka et al., 1995, Atherosclerosis 114(1):73-82).

An example of an animal model for human cancer in general includes, but is not limited to, spontaneously occurring tumors of companion animals (see, e.g., Vail & MacEwen, 2000, Cancer Invest 18(8):781-92). Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCRbeta and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3): 1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63). An example of an animal model for neurofibromatosis includes, but is not limited to, mutant NF1 mice (see, e.g., Cichowski et al., 1996, Semin Cancer Biol 7(5):291-8). Examples of animal models for retinoblastoma include, but are not limited to, transgenic mice that expression the simian virus 40 T antigen in the retina (see, e.g., Howes et al., 1994, Invest Opthalmol V is Sci 35(2):342-51 and Windle et al, 1990, Nature 343(6259): 665-9) and inbred rats (see, e.g., Nishida et al., 1981, Curr Eye Res 1(1):53-5 and Kobayashi et al., 1982, Acta Neuropathol (Berl) 57(2-3):203-8). Examples of animal models for Wilm's tumor include, but are not limited to, a WT1 knockout mice (see, e.g., Scharnhorst et al., 1997, Cell Growth Differ 8(2):133-43), a rat subline with a high incidence of neuphroblastoma (see, e.g., Mesfin & Breech, 1996, Lab Anim Sci 46(3):321-6), and a Wistar/Furth rat with Wilms' tumor (see, e.g., Murphy et al., 1987, Anticancer Res 7(4B):717-9).

4.2 Methods of Use

The invention encompasses methods of treating and preventing diseases or disorders ameliorated by the suppression of premature translation termination and/or nonsense-mediated mRNA decay in a patient which comprise administering to a patient in need of such treatment or prevention a therapeutically effective amount of a compound of the invention, or a pharmaceutically acceptable prodrug, solvate, metabolite, polymorph, salt, solvate, hydrate, or clathrate thereof.

In one embodiment, the present invention encompasses the treatment or prevention of any disease that is associated with a gene exhibiting premature translation termination and/or nonsense-mediated mRNA decay. In one embodiment, the disease is due, in part, to the lack of expression of the gene resulting from a premature stop codon. Specific examples of genes which may exhibit premature translation termination and/or nonsense-mediated mRNA decay and diseases associated with premature translation termination and/or nonsense-mediated mRNA decay are found in U.S. Patent Application No. 60/390,747, titled: Methods For Identifying Small Molecules That Modulate Premature Translation Termination And Nonsense Mediated mRNA Decay, filed Jun. 21, 2002, which is incorporated herein by reference in its entirety.

Diseases ameliorated by the suppression of premature translation termination and/or nonsense-mediated mRNA decay include, but are not limited to: a genetic disease, cancer, an autoimmune disease, a blood disease, a collagen disease, diabetes, a neurodegenerative disease, a proliferative disease, a cardiovascular disease, a pulmonary disease, an inflammatory disease or central nervous system disease.

Specific genetic diseases within the scope of the methods of the invention include, but are not limited to, amyloidosis, hemophilia, Alzheimer's disease, Tay Sachs disease, atherosclerosis, giantism, dwarfism, hypothyroidism, hyperthyroidism, aging, obesity, Parkinson's disease, Niemann Pick's disease, cystic fibrosis, muscular dystrophy, heart disease, kidney stones, ataxia-telangiectasia, familial hypercholesterolemia, retinitis pigmentosa, lysosomal storage disease, tuberous sclerosis, Duchenne muscular dystrophy, and Marfan syndrome. Both solid tumor and other cancers are included within the methods of the invention.

In another embodiment, the genetic disease is a central nervous system disease. In one embodiment the central nervous system disease is a neurodegenerative disease. In a preferred embodiment, the central nervous system disease is multiple sclerosis, muscular dystrophy, Duchenne muscular dystrophy, Alzheimer's disease, Tay Sachs disease, late infantile neuronal ceroid lipofuscinosis (LINCL) or Parkinson's disease.

In another embodiment, the genetic disease is cancer. In a preferred embodiment, the cancer is of the head and neck, eye, skin, mouth, throat, esophagus, chest, bone, lung, colon, sigmoid, rectum, stomach, prostate, breast, ovaries, kidney, liver, pancreas, brain, intestine, heart or adrenals.

In another preferred embodiment, the cancer is associated with tumor suppressor genes (see e.g. Garinis et al. 2002, Hum Gen 111: 115-117; Meyers et al. 1998, Proc. Natl. Acad. Sci. USA, 95: 15587-15591; Kung et al. 2000, Nature Medicine 6(12): 1335-1340. Such tumor suppressor genes include, but are not limited to, APC, ATM, BRAC1, BRAC2, MSH1, pTEN, Rb and p53.

In a particularly preferred embodiment, the tumor suppressor gene is the p53 gene. Nonsense mutations have been identified in the p53 gene and have been implicated in cancer. Several nonsense mutations in the p53 gene have been identified (see, e.g., Masuda et al., 2000, Tokai J Exp Clin Med. 25(2):69-77; Oh et al., 2000, Mol Cells 10(3):275-80; Li et al., 2000, Lab Invest. 80(4):493-9; Yang et al., 1999, Zhonghua Zhong Liu Za Zhi 21(2):114-8; Finkelstein et al., 1998, Mol Diagn. 3(1):37-41; Kajiyama et al., 1998, Dis Esophagus. 11(4):279-83; Kawamura et al., 1999, Leuk Res. 23(2): 115-26; Radig et al., 1998, Hum Pathol. 29(11):1310-6; Schuyer et al., 1998, Int J Cancer 76(3):299-303; Wang-Gohrke et al., 1998, Oncol Rep. 5(1):65-8; Fulop et al., 1998, J Reprod Med. 43(2):119-27; Ninomiya et al., 1997, J Dermatol Sci. 14(3):173-8; Hsieh et al., 1996, Cancer Lett. 100 (1-2): 107-13; Rall et al., 1996, Pancreas. 12(1):10-7; Fukutomi et al., 1995, Nippon Rinsho. 53(11):2764-8; Frebourg et al., 1995, Am J Hum Genet. 56(3):608-15; Dove et al., 1995, Cancer Surv. 25:335-55; Adamson et al., 1995, Br J Haematol. 89(1):61-6; Grayson et al., 1994, Am J Pediatr Hematol Oncol. 16(4):341-7; Lepelley et al., 1994, Leukemia. 8(8): 1342-9; McIntyre et al., 1994, J Clin Oncol. 12(5):925-30; Horio et al., 1994, Oncogene. 9(4):1231-5; Nakamura et al., 1992, Jpn J Cancer Res. 83(12):1293-8; Davidoff et al., 1992, Oncogene. 7(1):127-33; and Ishioka et al., 1991, Biochem Biophys Res Commun. 177(3):901-6; the disclosures of which are hereby incorporated by reference in their entireties). Any disease associated with a p53 gene encoding a premature translation codon including, but not limited to, the nonsense mutations described in the references cited above, can be treated or prevented by compounds of formula I and II without being limited by theory these compounds mediate premature translation termination and/or nonsense-mediated mRNA decay.

In other embodiments, diseases to be treated or prevented by administering to a patient in need thereof an effective amount of a compound of formula I or II include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, chronic lymphocytic leukemia, hairy cell leukemia, or multiple myeloma. See e.g., *Harrison's*

*Principles of Internal Medicine*, Eugene Braunwald et al., eds., pp. 491-762 (15th ed. 2001).

In a preferred embodiment, the invention encompasses a method of treating or preventing a disease ameliorated by modulation of premature translation termination and/or nonsense-mediated mRNA decay, or ameliorating one or more symptoms associated therewith comprising contacting a cell with an effective amount of a compound of formula I and II. Cells encompassed by the present methods include animal cells, mammalian cells, bacterial cells, plant cells and virally infected cells. In one embodiment, the nonsense codon was present in the progenitor DNA. In another embodiment, the nonsense codon resulted from mutagenesis.

In a preferred embodiment, it is first determined that the patient is suffering from a disease associate with premature translation termination and/or nonsense-mediated mRNA decay. In another embodiment, the patient has undergone a screening process to determine the presence of a nonsense mutation comprising the steps of screening a subject, or cells extracted therefrom, by an acceptable nonsense mutation screening assay. In a preferred embodiment, the DNA of the patient can be sequenced or subject to Southern Blot, polymerase chain reaction (PCR), use of the Short Tandem Repeat (STR), or polymorphic length restriction fragments (RFLP) analysis to determine if a nonsense mutation is present in the DNA of the patient. Alternatively, it can be determined if altered levels of the protein with the nonsense mutation are expressed in the patient by western blot or other immunoassays. In another embodiment, the patient is an unborn child who has undergone screening in utero for the presence of a nonsense mutation. Administration of a compound of formula I or II can occur either before or after birth. In a related embodiment, the therapy is personalized in that the patient is screened for a nonsense mutation screening assay and treated by the administration of one or more compounds of the invention; particularly, the patient may be treated with a compound particularly suited for the mutations in question; e.g., depending upon the disease type, cell type, and the gene in question. Such methods are well known to one of skill in the art.

In another embodiment, the cells (e.g., animal cells, mammalian cells, bacterial cells, plant cells and virally infected cells) are screened for premature translation termination and/or nonsense-mediated mRNA decay with a method such as that described above (i.e., the DNA of the cell can be sequenced or subjected to Southern Blot, polymerase chain reaction (PCR), use of the Short Tandem Repeat (STR), or polymorphic length restriction fragments (RFLP) analysis to determine if a nonsense mutation is present in the DNA of the cell).

Specific methods of the invention further comprise the administration of an additional therapeutic agent (i.e. a therapeutic agent other than a compound of the invention). In certain embodiments of the present invention, the compounds of the invention can be used in combination with at least one other therapeutic agent. Therapeutic agents include, but are not limited to non-opioid analgesics; non-steroid anti-inflammatory agents; antiemetics; β-adrenergic blockers; anticonvulsants; antidepressants; $Ca^{2+}$-channel blockers; anticancer agent and mixtures thereof.

In certain embodiments, the compounds of formula I and II can be administered or formulated in combination with anticancer agents. Suitable anticancer agents for use in combination with the compounds of the invention include, but are not limited to, alkylating agents; nitrogen mustards; folate antagonists; purine antagonists; pyrimidine antagonists; spindle poisons; topoisomerase inhibitors; apoptosis inducing agents; angiogenesis inhibitors; podophyllotoxins; nitrosoureas; cisplatin; carboplatin; interferon; asparaginase; tamoxifen; leuprolide; flutamide; megestrol; mitomycin; bleomycin; doxorubicin; irinotecan and taxol.

In certain embodiments, the compounds of formula I and II can be administered or formulated in combination with antibiotics. In certain embodiments, the antibiotic is a macrolide (e.g., tobramycin (Tobi®)), a cephalosporin (e.g., cephalexin (Keflex®), cephradine (Velosef®), cefuroxime (Ceftin®, cefprozil (Cefzil®), cefaclor (Ceclor®), cefixime (Suprax® or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)). In a preferred embodiment, the antibiotic is active against *Pseudomonas aeruginosa*.

The compounds of the invention and the other therapeutics agent can act additively or, more preferably, synergistically. In a preferred embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent.

The magnitude of a prophylactic or therapeutic dose of a particular active ingredient of the invention in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 0.1 mg to about 2000 mg per day, 1 mg to about 1000 mg per day, 5 mg to about 500 mg per day, 10 mg to about 200 mg per day, or 1 mg to about 10 mg per day given as a single once-a-day dose, preferably as divided doses throughout a day. In one embodiment, the daily dose is administered in a single dose or in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 2000 mg per day as either a single dose or divided doses, depending on the patient's global response.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

The phrases "therapeutically effective amount", "prophylactically effective amount" and "therapeutically or prophylactically effective amount," as used herein encompass the above described dosage amounts and dose frequency schedules. Different therapeutically effective amounts may be applicable for different diseases and conditions, as will be readily known by those of ordinary skill in the art. Similarly, amounts sufficient to treat or prevent such diseases, but insufficient to cause, or sufficient to reduce, adverse effects associated with conventional therapies are also encompassed by the above described dosage amounts and dose frequency schedules.

4.3 Pharmaceutical Compositions

Pharmaceutical compositions and single unit dosage forms comprising a compound of the invention, or a pharmaceutically acceptable polymorph, prodrug, salt, solvate, hydrate, or clathrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient.

The composition, shape, and type of dosage forms of the invention will typically vary depending on their use. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1995).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

4.4 Synthesis and Preparation

The compounds of the invention can be obtained via standard, well-known synthetic methodology, see e.g. March, J. *Advanced Organic Chemistry; Reactions Mechanisms, and Structure,* 4th ed., 1992. Starting materials useful for preparing the compounds of the invention and intermediates therefor, are commercially available or can be prepared from commercially available materials using known synthetic methods and reagents. Compounds of formula I and II can be synthesized using the synthesis depicted in Scheme A, infra. Examples of the synthesis of certain hydroxylated 1,2,4-oxadiazole benzoic acid compounds of the invention are provided in Section 5, infra.

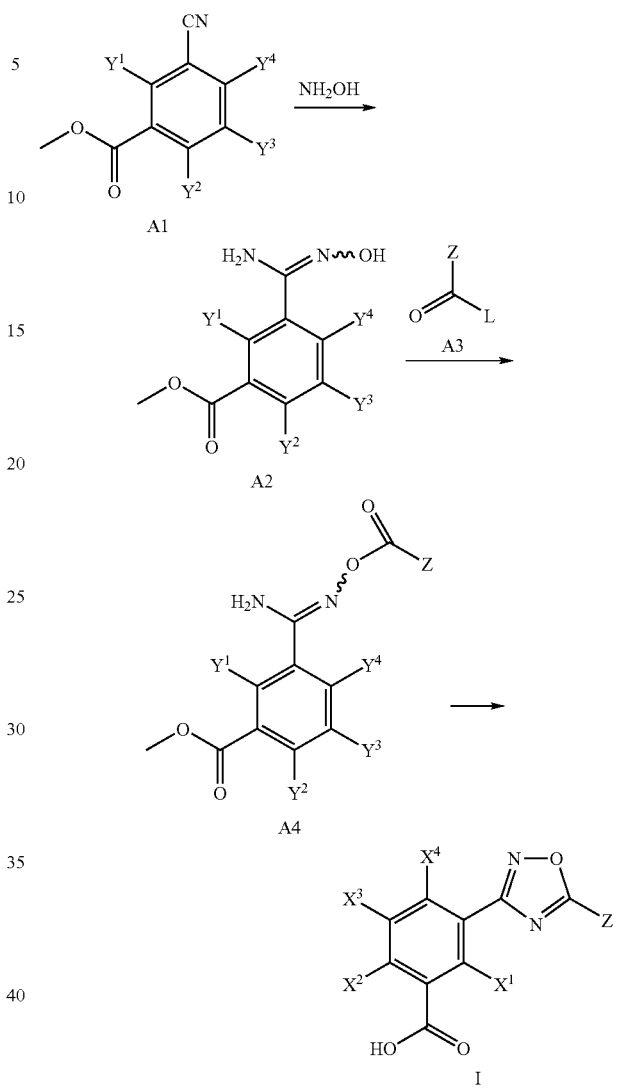

As depicted in Scheme A, The hydroxylated 1,2,4-oxadiazole benzoic acid compounds of the invention, I and II, have $X^1$, $X^2$, $X^3$ and $X^4$ independently as H or OH. The cyano compound A1 has $Y^1$, $Y^2$, $Y^3$ and $Y^4$ independently as H or $OCH_3$. The intended reaction depicted in Scheme A provides $X^n$=OH only if $Y^n$=$OCH_3$, where n is 1, 2, 3 or 4. The cyano compound A1 is hydroxyamidinated with hydroxyl amine. This reaction is usually performed in the presence of a base reagent, such as triethyl amine, potassium carbonate or diisopropylethylamine, in a solvent such as methanol, ethanol, tert-butanol, tetrahydrofuan or dimethylformamide, and temperatures ranging from ambient to the reflux temperature of the chosen solvent. The hydroxyamidine compound A2 is acylated with a reagent A3, wherein the group L represents some leaving groups, such as halo, imidazoyl, p-nitrophenol, etc. The reaction is usually carried out with a base reagent, such as triethyl amine or diisopropylethylamine, in a solvent such as dichloromethane, tetahydrofuan or dimethylformaide. An alternative method, the acylation is conveniently carried out under usual ester linkage formation reactions, wherein the group L represents hydroxy, using diisopropylcarbodiimide or equivalents such as benzotriazole-1-yl-oxytris-pyrrolidino-phosphonium hexafluorophosphate, bromo-tris-pyrrolidino-phosphonium hexafluorophosphate, 1-ethyl-3-(3-dimethylaminopropyl) carbodiimide hydrochloride without or with diisopropylethylamine. The ring-closure on the acylated compound A4 can be accomplished with or without a base reagent such as triethyl amine or diisopropylethylamine, in a solvent such as dichloromethane, tetrahydrofuran, toluene or dimethylformaide, and temperatures ranging from ambient to the reflux temperature of the chosen solvent.

5. EXAMPLES

The following examples employ methodology which can be used to prepare all of the compounds embodied in this invention, provided the appropriate reagents and substrates are utilized, and minor variations of the described conditions are maintained. Such variations would be easily performed by one of skill in the art without undue experimentation given the description below.

5.1 Example 1

Preparation of 5-[5-(2-fluorophenyl)-[1,2,4]oxadiazol-3-yl]-2-hydroxybenzoic acid

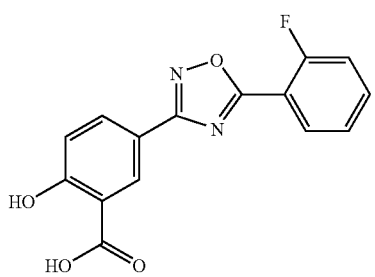

5-[5-(2-fluorophenyl)-[1,2,4]oxadiazol-3-yl]-2-hydroxybenzoic acid was prepared by the reaction depicted in Scheme B, infra. 1 g of methyl 5-cyano-2-methoxybenzoate was reacted with 1.2 molar equivalents of hydroxyl amine hydrochloride. To the hydroxyamidinated product was added 1.1 molar equivalents of 2-fluorobenzoyl chloride. The acylated product was reacted with boron bromide in dry dichloromethane to yield 40 mg of the O-demethylated product, 5-[5-(2-fluorophenyl)-[1,2,4]oxadiazol-3-yl]-2-hydroxybenzoic acid.

Scheme B

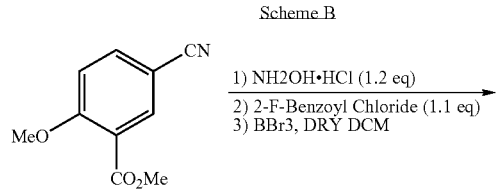

1) NH2OH•HCl (1.2 eq)
2) 2-F-Benzoyl Chloride (1.1 eq)
3) BBr3, DRY DCM

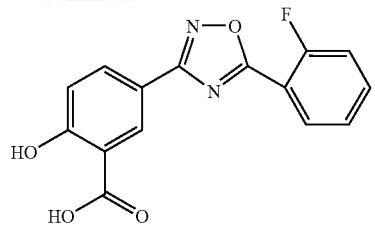

5.2 Example 2

Preparation of 3-[5-(2-fluorophenyl)-[1,2,4]oxadiazol-3-yl]-5-hydroxybenzoic acid

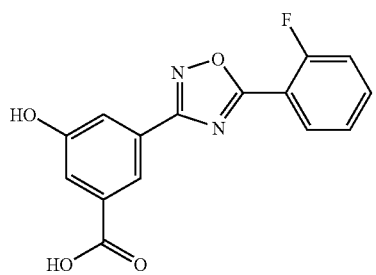

3-[5-(2-fluorophenyl)-[1,2,4]oxadiazol-3-yl]-5-hydroxybenzoic acid was prepared by the reactions depicted in Scheme C, infra. The C1 ester is converted into C2 by ester hydrolysis or saponification. 1.7 g of C2 was reacted for 2 days with 1.1 molar equivalents of ammonium chloride, 2 molar equivalents of EDCl, 2 molar equivalents of HOBt, 4 molar equivalents of DIPEA in 15 ml of DMF to provide C3 in 58% yield. 1 g of C3 was reacted for 2 hours between 0° C. and ambient temperature with 1 molar equivalent of cyanuric chloride in 10 ml DMF to provide C4 in 87% yield. 230 mg of C4 was reacted with 2 molar equivalents hydroxyl amine (50% aqueous solution) in 10 ml t-butanol with 1.1 molar equivalents triethylamine and 1.1 molar equivalents of 2-fluoro-benzoyl chloride. This reaction was immediately followed by the addition of boron bromide to provide 100 mg of C5, 3-[5-(2-fluorophenyl)-[1,2,4]oxadiazol-3-yl]-5-hydroxybenzoic acid.

Scheme C

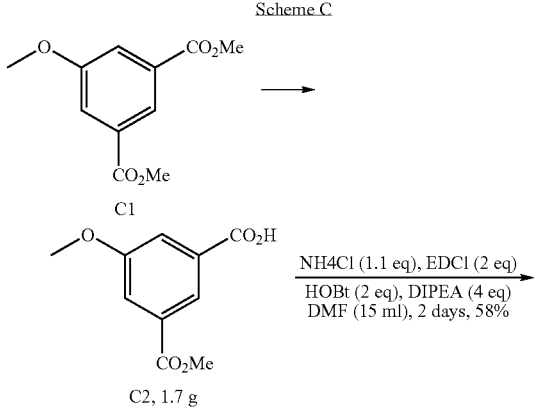

-continued

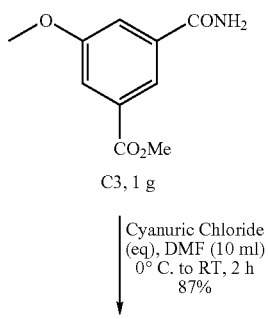

C3, 1 g

| Cyanuric Chloride
| (eq), DMF (10 ml)
| 0° C. to RT, 2 h
| 87%

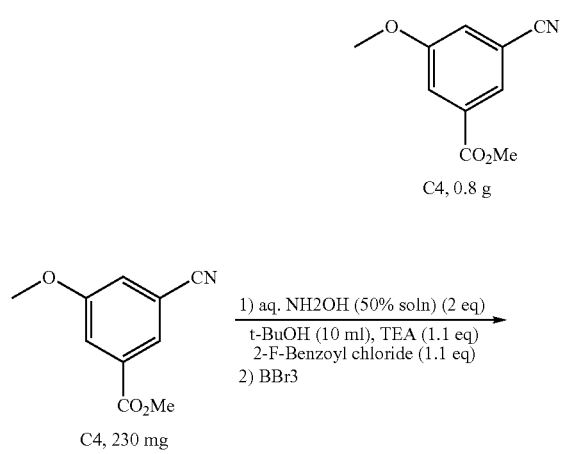

C4, 0.8 g

C4, 230 mg 1) aq. NH2OH (50% soln) (2 eq)
t-BuOH (10 ml), TEA (1.1 eq)
2-F-Benzoyl chloride (1.1 eq)
2) BBr3

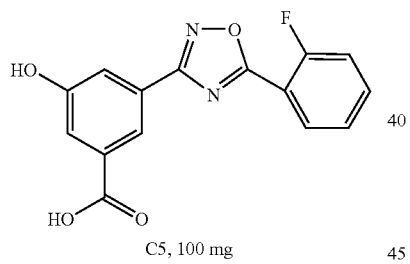

C5, 100 mg 5.3 Example 3

Preparation of 3-[5-(2-fluorophenyl)-[1,2,4]oxadiazol-3-yl]-4-hydroxybenzoic acid

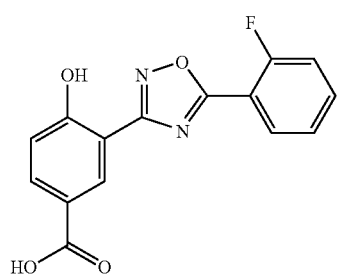

3-[5-(2-fluorophenyl)-[1,2,4]oxadiazol-3-yl]-4-hydroxybenzoic acid was prepared by the reactions depicted in Scheme D, infra. 1 g of D1 was reacted with 2 molar equivalents of hydroxylamine (50% aqueous solution) and 1 molar equivalent of 2-fluoro-benzoyl chloride in t-butanol to provide D2 in 46% yield. 200 mg of D2 was reacted with 3 molar equivalents of boron bromide in 10 ml dichloromethane for 2 hours at a temperature of between 0° C. to ambient temperature to provide in 55% yield the O-demethylated product D3 3-[5-(2-fluorophenyl)-[1,2,4]oxadiazol-3-yl]-4-hydroxybenzoic acid. The product of the reaction was analyzed by NMR, LCMS and HPLC.

Scheme D

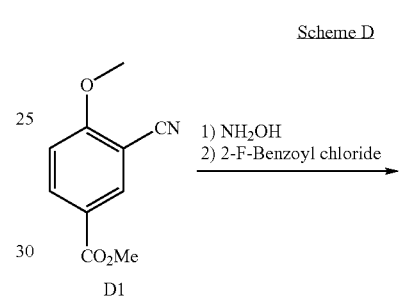

1) NH2OH
2) 2-F-Benzoyl chloride

D1

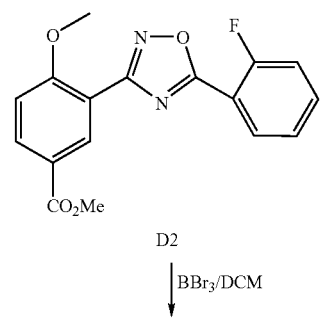

D2

BBr3/DCM

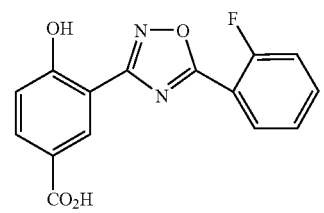

D3

The following compounds are prepared using the procedures described in Example 3, Scheme D and elsewhere as described herein.

| Compound | Compound Name | Mass [M + H] |
|---|---|---|
| 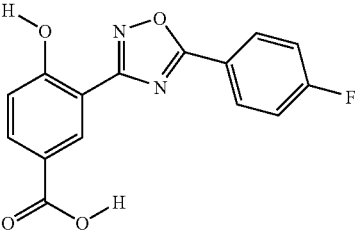 | 3-[5-(4-Fluoro-phenyl)-[1,2,4]oxadiazol-3-yl]-4-hydroxy-benzoic acid | 301 |
| 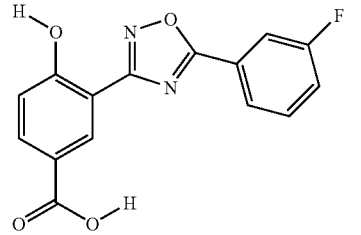 | 3-[5-(3-Fluoro-phenyl)-[1,2,4]oxadiazol-3-yl]-4-hydroxy-benzoic acid | 301 |
| 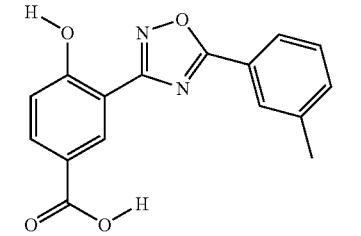 | 4-Hydroxy-3-(5-m-tolyl-[1,2,4]oxadiazol-3-yl)-benzoic acid | 297 |
| 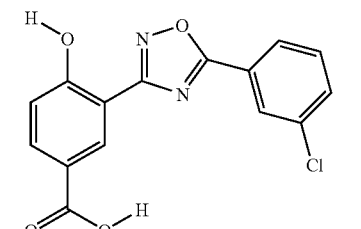 | 3-[5-(3-Chloro-phenyl)-[1,2,4]oxadiazol-3-yl]-4-hydroxy-benzoic acid | 317 |
| 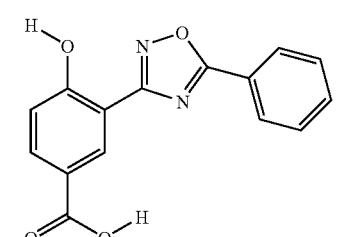 | 4-Hydroxy-3-(5-phenyl-[1,2,4]oxadiazol-3-yl)-benzoic acid | 283 |
| 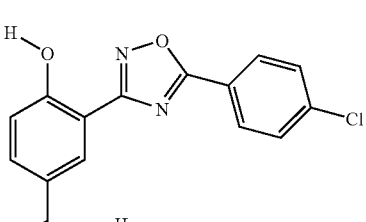 | 3-[5-(4-Chloro-phenyl)-[1,2,4]oxadiazol-3-yl]-4-hydroxy-benzoic acid | 317 |

-continued

| Compound | Compound Name | Mass [M + H] |
|---|---|---|
| | 3-[5-(2-Chloro-phenyl)-[1,2,4]oxadiazol-3-yl]-4-hydroxy-benzoic acid | 317 |
| | 4-Hydroxy-3-[5-(2-hydroxy-phenyl)-[1,2,4]oxadiazol-3-yl]-benzoic acid | 299 |
| | 3-[5-(3-Bromo-phenyl)-[1,2,4]oxadiazol-3-yl]-4-hydroxy-benzoic acid | 361 |
| | 3-[5-(4-tert-Butyl-phenyl)-[1,2,4]oxadiazol-3-yl]-4-hydroxy-benzoic acid | 339 |
| | 3-(5-Ethyl-[1,2,4]oxadiazol-3-yl)-4-hydroxy-benzoic acid | 235 |
| | 3-[5-(2,4-Difluoro-phenyl)-[1,2,4]oxadiazol-3-yl]-4-hydroxy-benzoic acid | 319 |

-continued

| Compound | Compound Name | Mass [M + H] |
|---|---|---|
| | 3-[5-(2,4-Dichloro-5-fluoro-phenyl)-[1,2,4]oxadiazol-3-yl]-4-hydroxy-benzoic acid | 369 |
| | 3-[5-(4-Cyano-phenyl)-[1,2,4]oxadiazol-3-yl]-4-hydroxy-benzoic acid | 308 |
| | 3-[5-(4-Dimethylamino-phenyl)-[1,2,4]oxadiazol-3-yl]-4-hydroxy-benzoic acid | 326 |
| | 3-[5-(5-Bromo-pyridin-3-yl)-[1,2,4]oxadiazol-3-yl]-4-hydroxy-benzoic acid | 362 |
| | 3-[5-(2,3-Difluoro-phenyl)-[1,2,4]oxadiazol-3-yl]-4-hydroxy-benzoic acid | 319 |
| | 3-[5-(5-Chloro-pyridin-3-yl)-[1,2,4]oxadiazol-3-yl]-4-hydroxy-benzoic acid | 318 |

-continued

| Compound | Compound Name | Mass [M + H] |
|---|---|---|
| | 4-Hydroxy-3-[5-(4-hydroxy-phenyl)-[1,2,4]oxadiazol-3-yl]-benzoic acid | 299 |
| | 4-Hydroxy-3-(5-phenoxymethyl-[1,2,4]oxadiazol-3-yl)-benzoic acid | 313 |
| | 4-Hydroxy-3-[5-(3-trifluoromethyl-phenyl)-[1,2,4]oxadiazol-3-yl]-benzoic acid | 351 |
| | 3-[5-(2,5-Difluoro-phenyl)-[1,2,4]oxadiazol-3-yl]-4-hydroxy-benzoic acid | 319 |
| | 3-[5-(3,5-Difluoro-phenyl)-[1,2,4]oxadiazol-3-yl]-4-hydroxy-benzoic acid | 319 |
| | 3-[5-(3,5-Bis-trifluoromethyl-phenyl)-[1,2,4]oxadiazol-3-yl]-4-hydroxy-benzoic acid | 419 |

-continued

| Compound | Compound Name | Mass [M + H] |
|---|---|---|
| | 3-[5-(2-Fluoro-4-trifluoromethyl-phenyl)-[1,2,4]oxadiazol-3-yl]-4-hydroxy-benzoic acid | 369 |
| | 3-[5-(2-Fluoro-5-trifluoromethyl-phenyl)-[1,2,4]oxadiazol-3-yl]-4-hydroxy-benzoic acid | 369 |
| | 4-Hydroxy-3-[5-(2,4,6-trichloro-phenyl)-[1,2,4]oxadiazol-3-yl]-benzoic acid | 385 |
| | 3-[5-(3-Cyano-phenyl)-[1,2,4]oxadiazol-3-yl]-4-hydroxy-benzoic acid | 308 |
| | 3-(5-Biphenyl-4-yl-[1,2,4]oxadiazol-3-yl)-4-hydroxy-benzoic acid | 359 |
| | 3-[5-(2-Fluoro-3-trifluoromethyl-phenyl)-[1,2,4]oxadiazol-3-yl]-4-hydroxy-benzoic acid | 369 |

-continued

| Compound | Compound Name | Mass [M + H] |
|---|---|---|
|  | 4-Hydroxy-3-(5-naphthalen-1-yl-[1,2,4]oxadiazol-3-yl)-benzoic acid | 333 |
|  | 4-Hydroxy-3-[5-(3-nitro-phenyl)-[1,2,4]oxadiazol-3-yl]-benzoic acid | 328 |
|  | 3-(5-Butyl-[1,2,4]oxadiazol-3-yl)-4-hydroxy-benzoic acid | 263 |
|  | 4-Hydroxy-3-[5-(2-methoxy-phenyl)-[1,2,4]oxadiazol-3-yl]-benzoic acid | 313 |
|  | 3-(5-But-2-enyl-[1,2,4]oxadiazol-3-yl)-4-hydroxy-benzoic acid | 261 |

-continued

| Compound | Compound Name | Mass [M + H] |
|---|---|---|
| | 4-Hydroxy-3-[5-(4-trifluoromethyl-phenyl)-[1,2,4]oxadiazol-3-yl]-benzoic acid | 351 |
| | 4-Hydroxy-3-[5-(3-sulfo-phenyl)-[1,2,4]oxadiazol-3-yl]-benzoic acid | 363 |
| | 3-[5-(4-Bromo-phenyl)-[1,2,4]oxadiazol-3-yl]-4-hydroxy-benzoic acid | 361 |
| | 3-(5-Benzyl-[1,2,4]oxadiazol-3-yl)-4-hydroxy-benzoic acid | 297 |
| | 4-Hydroxy-3-[5-(4-nitro-phenyl)-[1,2,4]oxadiazol-3-yl]-benzoic acid | 328 |
| | 4-Hydroxy-3-(5-isopropyl-[1,2,4]oxadiazol-3-yl)-benzoic acid | 249 |

5.4 Example 4

Preparation of 3-[5-(2-Fluoro-phenyl)-[1,2,4]oxadiazol-3-yl]-2-hydroxy-benzoic acid

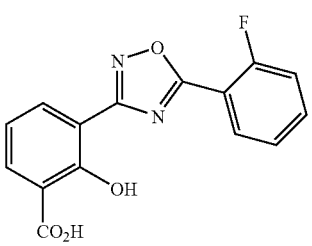

To a solution of 2-methoxy benzoic acid (15.7 g, 100 mmol) in acetic acid (250 mL) was added N-bromosuccinimide (18.6 g, 100 mmol). The reaction mixture was cooled down to 0° C., to which trifluoromethanesulfonic acid (18 mL, 200 mmol) was added. The mixture was stirred at room temperature for 16 hours and the solvents were removed under reduced pressure. The oily residue was dissolved in ethyl acetate and washed with water three times. The organic layer was dried over $Na_2SO_4$ and concentrated to give the crude product 1 (22 g, 95%) as a white solid.

To a solution of 1 (22 g, 95.2 mmol) in conc $H_2SO_4$ (150 mL) at −10° C. was added a solution of fuming nitric acid (8 mL, 190 mmol) in conc $H_2SO_4$ (40 mL) dropwisely to keep the internal temperature below 0° C. After the addition, the reaction was stirred for 10 min at 0° C. then poured into ice. The white precipitate was filtered, rinsed with water and dried to give the crude product 2 (25 g, 95%) as a white solid.

To a solution of 2 (25 g, 90.6 mmol) in methanol (80 mL) under nitrogen atmosphere was added $Pd(OH)_2$ on carbon (20%, 1.5 g). The reaction vessel was charged with hydrogen gas and shaken at 45 psi for 4 hours. The mixture was filtered through celite and concentrated to give 3 (15 g, 99%) as a yellow oil.

To a solution of 3 (7.5 g, 45 mmol) in 6N HCl (30 mL) and ethanol (60 mL) at −0° C. was added a solution of $NaNO_2$ (3.3 g, 48 mmol) in water (10 mL) dropwisely to keep the internal temperature below 5° C. After the addition, NaI (7 g, 48 mmol) was added. The reaction mixture was stirred at 0° C. for 1 hour, then at room temperature for 16 hours before it was poured into water. The white precipitate was filtered and rinsed with water to give 4 (3.7 g, 30%) as a white solid.

To a solution of 4 (3.7 g, 13.3 mmol) in DMF (25 mL) was added $K_2CO_3$ (2.8 g, 20 mmol). The mixture was stirred at room temperature for 30 min before iodomethane (1.25 mL, 20 mmol) was added. After stirring for 4 hours, the reaction was poured into water and extracted with ethyl acetate three times. The organic layer was washed with brine, dried over $Na_2SO_4$ and concentrated. The residue was purified by flash chromatography to give product 5 (3.7 g, 95%) as a white solid.

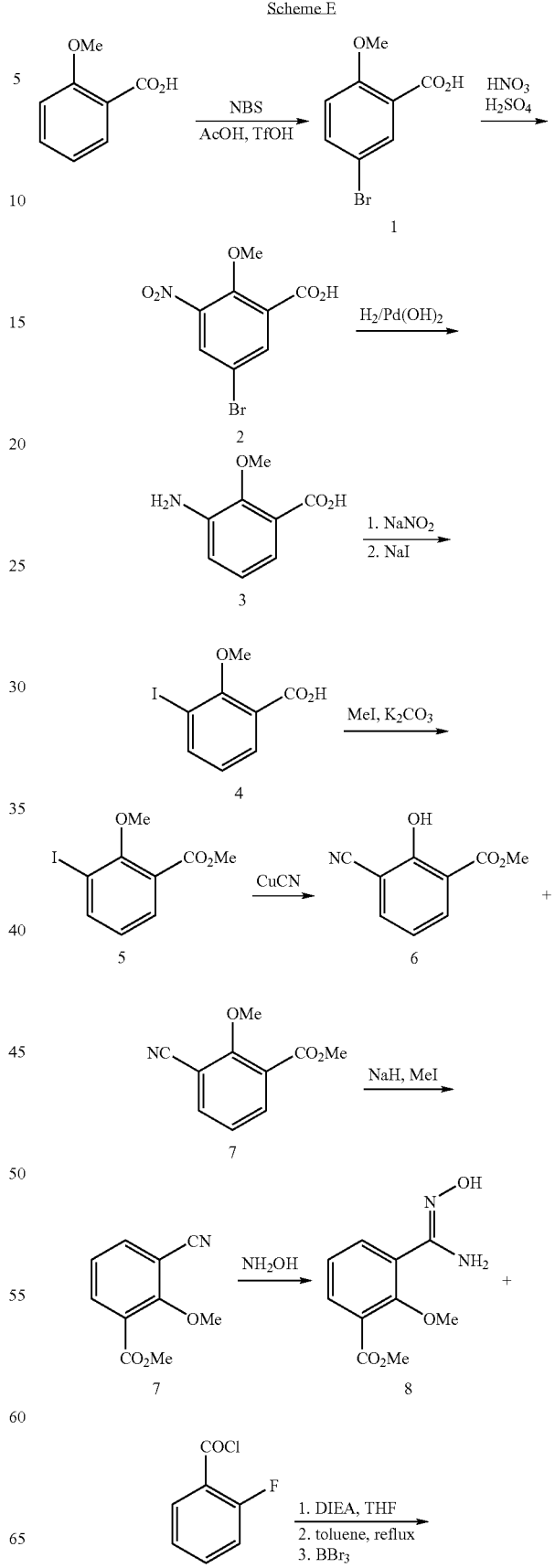

Scheme E

-continued

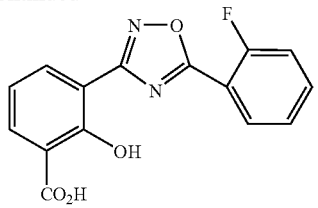

9

To a solution of 5 (9 g, 29.4 mmol) in pyridine (100 mL) purged with nitrogen was added CuCN (3.2 g, 35.3 mmol). After refluxing for 4 hours, the mixture poured into water and extracted with ethyl acetate three times. The organic layer was washed with brine, dried over $Na_2SO_4$ and concentrated. The residue contains a mixture of compound 6 and 7. To this mixture in DMF (50 mL) was added $K_2CO_3$ (2.8 g, 20 mmol) followed by iodomethane (1.25 mL, 20 mmol). The reaction was heated at 50° C. for 16 hours, then poured into water and extracted with ethyl acetate three times. The organic layer was washed with brine, dried over $Na_2SO_4$ and concentrated. The residue was purified by flash chromatography to give product 7 (4 g, 66%) as a white solid To a solution of 7 (0.7 g, 3.66 mmol) in THF (15 mL) was added 50% aqueous hydroxylamine (0.3 mL, 4.4 mmol) at room temperature. The reaction mixture was reflux for 8 h and the solvents were removed under reduced pressure. The oily residue was dissolved in 20/80 ethanol/toluene and then concentrated again to give the crude product 8 as a white solid.

To a solution of 8 (0.45 g, 2.01 mmol) in anhydrous THF (20 mL) was added diisopropylethylamine (0.5 mL, 3 mmol) followed by 2-fluorobenzoyl chloride (0.3 mL, 2.61 mmol). The reaction mixture was stirred for 2 h at room temperature, then diluted with ethyl acetate. The mixture was washed with water twice followed by brine. The organic layer was dried over $Na_2SO_4$ and concentrated. The residue was suspended in toluene (25 mL) and heated under reflux for 4 h at 130° C. using a Dean-Stark apparatus. The reaction mixture was cooled to room temperature and then stirred for 18 h. The solvent was removed under reduced pressure. The residue was purified by flash chromatography to give the desired oxadiazole (330 mg, 50%, 3 steps) as a white solid.

To a solution of the oxadiazole (72 mg, 0.22 mmol) in anhydrous $CH_2Cl_2$ (2 mL) was added $BBr_3$ (0.085 mL, 0.88 mmol). The reaction mixture was stirred for 2 h at 35° C., then quenched by the careful addition of water. The white precipitate was filtered, washed with water and dried to give the desired product 9 (59 mg, 90%) as a white solid.

The following compounds are prepared using the procedures described in Example 4, Scheme E and elsewhere as described herein.

| Compound | Compound Name | Mass [M + H] |
|---|---|---|
| | 3-[5-(3-Fluoro-phenyl)-[1,2,4]oxadiazol-3-yl]-2-hydroxy-benzoic acid | 301 |
| | 3-[5-(4-Fluoro-phenyl)-[1,2,4]oxadiazol-3-yl]-2-hydroxy-benzoic acid | 301 |
| | 2-Hydroxy-3-(5-p-tolyl-[1,2,4]oxadiazol-3-yl)-benzoic acid | 297 |

-continued

| Compound | Compound Name | Mass [M + H] |
|---|---|---|
|  | 3-[5-(4-tert-Butyl-phenyl)-[1,2,4]oxadiazol-3-yl]-2-hydroxy-benzoic acid | 339 |
|  | 2-Hydroxy-3-[5-(4-methoxy-phenyl)-[1,2,4]oxadiazol-3-yl]-benzoic acid | 313 |
|  | 3-[5-(2-Chloro-phenyl)-[1,2,4]oxadiazol-3-yl]-2-hydroxy-benzoic acid | 317 |
|  | 3-[5-(3-Chloro-phenyl)-[1,2,4]oxadiazol-3-yl]-2-hydroxy-benzoic acid | 317 |
|  | 3-[5-(3-Chloro-phenyl)-[1,2,4]oxadiazol-3-yl]-2-hydroxy-benzoic acid | 317 |
|  | 2-Hydroxy-3-(5-m-tolyl-[1,2,4]oxadiazol-3-yl)-benzoic acid | 297 |

-continued

| Compound | Compound Name | Mass [M + H] |
|---|---|---|
| | 2-Hydroxy-3-(5-phenyl-[1,2,4]oxadiazol-3-yl)-benzoic acid | 283 |
| | 3-[5-(2,4-Dichloro-5-fluoro-phenyl)-[1,2,4]oxadiazol-3-yl]-2-hydroxy-benzoic acid | 369 |
| | 2-Hydroxy-3-[5-(3-trifluoromethyl-phenyl)-[1,2,4]oxadiazol-3-yl]-benzoic acid | 351 |
| | 2-Hydroxy-3-[5-(4-trifluoromethyl-phenyl)-[1,2,4]oxadiazol-3-yl]-benzoic acid | 351 |
| | 2-Hydroxy-3-[5-(2-methoxy-phenyl)-[1,2,4]oxadiazol-3-yl]-benzoic acid | 313 |
| | 2-Hydroxy-3-[5-(3-methoxy-phenyl)-[1,2,4]oxadiazol-3-yl]-benzoic acid | 313 |

5.5 Example 5

Preparation of 1,2,4-oxadiazole benzoic acid compounds

The following 1,2,4-oxadiazole benzoic acid compounds can be prepared using methods as described in Examples 1, 2 and 3. Compounds are analyzed by a LC/MS using Electrospray Ionization (ESI).

| Compound | Compound Name | Mass [M + H] |
|---|---|---|
|  | 3-[5-(2-fluorophenyl)-[1,2,4]oxadiazol-3-yl]-2-hydroxybenzoic acid | 301.1 |
|  | 5-[5-(2-fluorophenyl)-[1,2,4]oxadiazol-3-yl]-2-hydroxybenzoic acid | 301.1 |
|  | 3-[5-(2-fluorophenyl)-[1,2,4]oxadiazol-3-yl]-5-hydroxybenzoic acid | 301.1 |
|  | 3-[5-(2-fluorophenyl)-[1,2,4]oxadiazol-3-yl]-4-hydroxybenzoic acid | 301.1 |

-continued

| Compound | Compound Name | Mass [M + H] |
|---|---|---|
| | 3-[5-(2-fluorophenyl)-[1,2,4]oxadiazol-3-yl]-2,6-dihydroxybenzoic acid | 317.1 |
| | 3-[5-(2-fluorophenyl)-[1,2,4]oxadiazol-3-yl]-2,5-dihydroxybenzoic acid | 317.1 |
| | 3-[5-(2-fluorophenyl)-[1,2,4]oxadiazol-3-yl]-2,4-dihydroxybenzoic acid | 317.1 |
| | 5-[5-(2-fluorophenyl)-[1,2,4oxadiazol-3-yl]-2,3-dihydroxybenzoic acid | 317.1 |
| | 5-[5-(2-fluorophenyl)-[1,2,4]oxadiazol-3-yl]-2,4-dihydroxybenzoic acid | 317.1 |

-continued

| Compound | Compound Name | Mass [M + H] |
|---|---|---|
| | 3-[5-(2-fluorophenyl)-[1,2,4]oxadiazol-3-yl]-4,5-dihydroxybenzoic acid | 317.1 |
| | 3-[5-(2-fluorophenyl)-[1,2,4]oxadiazol-3-yl]-2,5,6-trihydroxybenzoic acid | 333.0 |
| | 3-[5-(2-fluorophenyl)-[1,2,4]oxadiazol-3-yl]-2,4,6-trihydroxybenzoic acid | 333.0 |
| | 3-[5-(2-fluorophenyl)-[1,2,4]oxadiazol-3-yl]-2,4,5-trihydroxybenzoic acid | 333.0 |
| | 5-[5-(2-fluorophenyl)-[1,2,4]oxadiazol-3-yl]-2,3,4-trihydroxybenzoic acid | 333.0 |

-continued

| Compound | Compound Name | Mass [M + H] |
|---|---|---|
|  | 3-[5-(2-fluorophenyl)-[1,2,4]oxadiazol-3-yl]-2,4,5,6-tetrahydroxybenzoic acid | 349.0 |

5.6 Example 6

Identification and Characterization of Compounds that Promote Nonsense Suppression and/or Modulate Translation Termination The assays described above in Section 4.2 can be used in two high throughput screens. Compounds can be screened in the cell-based and biochemical assays. Compounds can be tested, resynthesized and tested again to confirm chemical structures. Compounds can be characterized further with the in vitro luciferase nonsense suppression assay. To ensure that the observed nonsense suppression activity of the selected compounds is not limited to the rabbit reticulocyte assay system, HeLa cell extract can be prepared and optimized (Lie & Macdonald, 1999, *Development* 126(22):4989-4996 and Lie & Macdonald, 2000, *Biochem. Biophys. Res. Commun.* 270(2):473-481).

5.7 Example 7

Characterization of Compounds that Increase Nonsense Suppression and Produce Functional Protein Compounds of the invention can be demonstrated to increase the level of nonsense suppression in the biochemical assay over untreated extracts. To determine whether compounds also function in vivo, a stable cell line harboring the UGA nonsense-containing luciferase gene can be treated with selected compounds. Cells cells can be grown in standard medium supplemented with 1% penicillin-streptomycin (P/S) and 10% fetal bovine serum (FBS) to 70% confluency and split 1:1 the day before treatment. On the following day, cells can be trypsinized and 40,000 cells can be added to each well of a 96-well tissue culture dish. Serial dilutions of each compound can be prepared to generate a six-point dose response curve spanning 2 logs (30 μM to 0.3 μM). The final concentration of the DMSO solvent can be measured. Cells treated with 1% DMSO can serve as the background standard, and cells treated with gentamicin can serve as a positive control.

5.8 Example 8

Readthrough of Premature Termination Codons in Cell-Based Disease Models

To address the effects of the nonsense-suppressing compounds on mRNAs altered in specific inherited diseases, a bronchial epithelial cell line harboring a nonsense codon at amino acid 1282 (W1282X) can be treated with a compound of the invention (e.g., 20 μM) and CFTR function can be monitored as a cAMP-activated chloride channel using the SPQ assay (Yang et al., 1993, Hum Mol. Genet. 2(8):1253-1261 and Howard et al., 1996, Nat Med. 2(4):467-469). These experiments can show that cAMP treatment of these cells may result in an increase in SPQ fluorescence, consistent with stimulation of CFTR-mediated halide efflux. It would be expected that no increase in fluorescence would be observed when cells are not treated with compound or if the cells are not stimulated with cAMP. These results can indicate that the full-length CFTR expressed from this nonsense-containing allele following compound treatment also functions as a cAMP-stimulated anion channel, thus demonstrating that cystic fibrosis cell lines increase chloride channel activity when treated with a compound of the invention.

5.9 Example 9

Readthrough of Premature Termination Codons in the mdx Mouse

Similar to the procedure previously described (Barton-Davis et al., 1999, *J Clin Invest.* 104(4):375-381), a compound can be delivered by Alzet osmotic pumps implanted under the skin of anesthetized mice. Two doses of a compound of the invention can be administered. Gentamicin can serve as a positive control and pumps filled with solvent only can serve as the negative control. Pumps can be loaded with appropriate compound such that the calculated doses to which tissue was exposed are 10 μM and 20 μM. The gentamicin concentration can be calculated to achieve tissue exposure of approximately 200 μM. In an initial experiment, mice can be treated for 14 days, after which animals can be anesthetized with ketamine and exsanguinated. The tibialis anterior (TA) muscle of the experimental animals can then be excised, frozen, and used for immunofluorescence analysis of dystrophin incorporation into striated muscle. The presence of dystrophin in TA muscles can be detected by immunostaining, as described previously (Barton-Davis et al., 1999, *J Clin Invest.* 104(4):375-381).

5.10 Example 10

200 Mg Dosage Capsule

The table below illustrates a batch formulation and single dosage formulation for a 200 mg single dose unit, i.e., about 40 percent by weight.

Formulation for 200 mg capsule

| Material | Percent By Weight | Quantity (mg/tablet) | Quantity (kg/batch) |
|---|---|---|---|
| Compound of the invention | 40.0% | 200 mg | 16.80 kg |
| Pregelatinized Corn Starch, NF5 | 9.5% | 297.5 mg | 24.99 kg |
| Magnesium Stearate | 0.5% | 2.5 mg | 0.21 kg |
| Total | 100.0% | 500 mg | 42.00 kg |

The pregelatinized corn starch (SPRESS B-820) and compound of the invention components are passed through a 710 μm screen and then are loaded into a Diffusion Mixer with a baffle insert and blended for 15 minutes. The magnesium stearate is passed through a 210 μm screen and is added to the Diffusion Mixer. The blend is then encapsulated in a size #0 capsule, 500 mg per capsule (8400 capsule batch size) using a Dosator type capsule filling machine.

5.11 Example 11

100 Mg Oral Dosage Form

The table below illustrates a batch formulation and a single dose unit formulation containing 100 mg of a compound of the invention.

Formulation for 100 mg tablet

| Material | Percent by Weight | Quantity (mg/tablet) | Quantity (kg/batch) |
|---|---|---|---|
| compound of the invention | 40% | 100.00 | 20.00 |
| Microcrystalline Cellulose, NF | 53.5% | 133.75 | 26.75 |
| Pluronic F-68 Surfactant | 4.0% | 10.00 | 2.00 |
| Croscarmellose Sodium Type A, NF | 2.0% | 5.00 | 1.00 |
| Magnesium Stearate, NF | 0.5% | 1.25 | 0.25 |
| Total | 100.0% | 250.00 mg | 50.00 kg |

The microcrystalline cellulose, croscarmellose sodium, and compound of the invention components are passed through a #30 mesh screen (about 430μ to about 655μ). The Pluronic F-68® (manufactured by JRH Biosciences, Inc. of Lenexa, Kans.) surfactant is passed through a #20 mesh screen (about 457μ to about 1041μ). The Pluronic F-68® surfactant and 0.5 kgs of croscarmellose sodium are loaded into a 16 qt. twin shell tumble blender and are mixed for about 5 minutes. The mix is then transferred to a 3 cubic foot twin shell tumble blender where the microcrystalline cellulose is added and blended for about 5 minutes. The compound is added and blended for an additional 25 minutes. This pre-blend is passed through a roller compactor with a hammer mill attached at the discharge of the roller compactor and moved back to the tumble blender. The remaining croscarmellose sodium and magnesium stearate is added to the tumble blender and blended for about 3 minutes. The final mixture is compressed on a rotary tablet press with 250 mg per tablet (200,000 tablet batch size).

5.12 Example 12

Aerosal Dosage Form

A concentrate is prepared by combining a compound of the invention, and a 12.6 kg portion of the trichloromonofluoromethane in a sealed stainless steel vessel equipped with a high shear mixer. Mixing is carried out for about 20 minutes. The bulk suspension is then prepared in the sealed vessel by combining the concentrate with the balance of the propellants in a bulk product tank that is temperature controlled to 21° to 27° C. and pressure controlled to 2.8 to 4.0 BAR. 17 ml aerosol containers that have a metered valve which is designed to provide 100 inhalations of the composition of the invention. Each container is provided with the following:

| | |
|---|---|
| compound of the invention | 0.0141 g |
| trichloromonofluoromethane | 1.6939 g |
| dichlorodifluoromethane | 3.7028 g |
| dichlorotetrafluoroethane | 1.5766 g |
| total | 7.0000 g |

What is claimed is:
1. A compound, wherein the compound is selected from the group consisting of:
3-[5-(2-fluorophenyl)-[1,2,4]oxadiazol-3-yl]-2-hydroxybenzoic acid;
5-[5-(2-fluorophenyl)-[1,2,4]oxadiazol-3-yl]-2-hydroxybenzoic acid;
3-[5-(2-fluorophenyl)-[1,2,4]oxadiazol-3-yl]-5-hydroxybenzoic acid;
3-[5-(2-fluorophenyl)-[1,2,4]oxadiazol-3-yl]-4-hydroxybenzoic acid;
3-[5-(2-fluorophenyl)-[1,2,4]oxadiazol-3-yl]-2,6-dihydroxybenzoic acid;
3-[5-(2-fluorophenyl)-[1,2,4]oxadiazol-3-yl]-2,5-dihydroxybenzoic acid;
3-[5-(2-fluorophenyl)-[1,2,4]oxadiazol-3-yl]-2,4-dihydroxybenzoic acid;
5-[5-(2-fluorophenyl)-[1,2,4]oxadiazol-3-yl]-2,3-dihydroxybenzoic acid;
5-[5-(2-fluorophenyl)-[1,2,4]oxadiazol-3-yl]-2,4-dihydroxybenzoic acid;
3-[5-(2-fluorophenyl)-[1,2,4]oxadiazol-3-yl]-4,5-dihydroxybenzoic acid;
3-[5-(2-fluorophenyl)-[1,2,4]oxadiazol-3-yl]-2,5,6-trihydroxybenzoic acid;
3-[5-(2-fluorophenyl)-[1,2,4]oxadiazol-3-yl]-2,4,6-trihydroxybenzoic acid;
3-[5-(2-fluorophenyl)-[1,2,4]oxadiazol-3-yl]-2,4,5-trihydroxybenzoic acid;
5-[5-(2-fluorophenyl)-[1,2,4]oxadiazol-3-yl]-2,3,4-trihydroxybenzoic acid;
3-[5-(2-fluorophenyl)-[1,2,4]oxadiazol-3-yl]-2,4,5,6-tetrahydroxybenzoic acid;
3-[5-(4-Fluoro-phenyl)-[1,2,4]oxadiazol-3-yl]-4-hydroxy-benzoic acid;
3-[5-(3-Fluoro-phenyl)-[1,2,4]oxadiazol-3-yl]-4-hydroxy-benzoic acid;
4-Hydroxy-3-(5-m-tolyl-[1,2,4]oxadiazol-3-yl)-benzoic acid;
3-[5-(3-Chloro-phenyl)-[1,2,4]oxadiazol-3-yl]-4-hydroxy-benzoic acid;
4-Hydroxy-3-(5-phenyl-[1,2,4]oxadiazol-3-yl)-benzoic acid;

3-[5-(4-Chloro-phenyl)-[1,2,4]oxadiazol-3-yl]-4-hydroxy-benzoic acid;
3-[5-(2-Chloro-phenyl)-[1,2,4]oxadiazol-3-yl]-4-hydroxy-benzoic acid;
4-Hydroxy-3-[5-(2-hydroxy-phenyl)-[1,2,4]oxadiazol-3-yl]-benzoic acid;
3-[5-(3-Bromo-phenyl)-[1,2,4]oxadiazol-3-yl]-4-hydroxy-benzoic acid;
3-[5-(4-tert-Butyl-phenyl)-[1,2,4]oxadiazol-3-yl]-4-hydroxy-benzoic acid;
3-(5-Ethyl-[1,2,4]oxadiazol-3-yl)-4-hydroxy-benzoic acid;
3-[5-(2,4-Difluoro-phenyl)-[1,2,4]oxadiazol-3-yl]-4-hydroxy-benzoic acid;
3-[5-(2,4-Dichloro-5-fluoro-phenyl)-[1,2,4]oxadiazol-3-yl]-4-hydroxy-benzoic acid;
3-[5-(4-Cyano-phenyl)-[1,2,4]oxadiazol-3-yl]-4-hydroxy-benzoic acid;
3-[5-(4-Dimethylamino-phenyl)-[1,2,4]oxadiazol-3-yl]-4-hydroxy-benzoic acid;
3-[5-(5-Bromo-pyridin-3-yl)-[1,2,4]oxadiazol-3-yl]-4-hydroxy-benzoic acid;
3-[5-(2,3-Difluoro-phenyl)-[1,2,4]oxadiazol-3-yl]-4-hydroxy-benzoic acid;
3-[5-(5-Chloro-pyridin-3-yl)-[1,2,4]oxadiazol-3-yl]-4-hydroxy-benzoic acid;
4-Hydroxy-3-[5-(4-hydroxy-phenyl)-[1,2,4]oxadiazol-3-yl]-benzoic acid;
4-Hydroxy-3-(5-phenoxymethyl-[1,2,4]oxadiazol-3-yl)-benzoic acid;
4-Hydroxy-3-[5-(3-trifluoromethyl-phenyl)-[1,2,4]oxadiazol-3-yl]-benzoic acid;
3-[5-(2,5-Difluoro-phenyl)-[1,2,4]oxadiazol-3-yl]-4-hydroxy-benzoic acid;
3-[5-(3,5-Difluoro-phenyl)-[1,2,4]oxadiazol-3-yl]-4-hydroxy-benzoic acid;
3-[5-(3,5-Bis-trifluoromethyl-phenyl)-[1,2,4]oxadiazol-3-yl]-4-hydroxy-benzoic acid;
3-[5-(2-Fluoro-4-trifluoromethyl-phenyl)-[1,2,4]oxadiazol-3-yl]-4-hydroxy-benzoic acid;
3-[5-(2-Fluoro-5-trifluoromethyl-phenyl)-[1,2,4]oxadiazol-3-yl]-4-hydroxy-benzoic acid;
4-Hydroxy-3-[5-(2,4,6-trichloro-phenyl)-[1,2,4]oxadiazol-3-yl]-benzoic acid;
3-[5-(3-Cyano-phenyl)-[1,2,4]oxadiazol-3-yl]-4-hydroxy-benzoic acid;
3-(5-Biphenyl-4-yl-[1,2,4]oxadiazol-3-yl)-4-hydroxy-benzoic acid;
3-[5-(2-Fluoro-3-trifluoromethyl-phenyl)-[1,2,4]oxadiazol-3-yl]-4-hydroxy-benzoic acid;
4-Hydroxy-3-(5-naphthalen-1-yl-[1,2,4]oxadiazol-3-yl)-benzoic acid;
4-Hydroxy-3-[5-(3-nitro-phenyl)-[1,2,4]oxadiazol-3-yl]-benzoic acid;
3-(5-Butyl-[1,2,4]oxadiazol-3-yl)-4-hydroxy-benzoic acid;
4-Hydroxy-3-[5-(2-methoxy-phenyl)-[1,2,4]oxadiazol-3-yl]-benzoic acid;
3-(5-But-2-enyl-[1,2,4]oxadiazol-3-yl)-4-hydroxy-benzoic acid;
4-Hydroxy-3-[5-(4-trifluoromethyl-phenyl)-[1,2,4]oxadiazol-3-yl]-benzoic acid;
4-Hydroxy-3-[5-(3-sulfo-phenyl)-[1,2,4]oxadiazol-3-yl]-benzoic acid;
3-[5-(4-Bromo-phenyl)-[1,2,4]oxadiazol-3-yl]-4-hydroxy-benzoic acid;
3-(5-Benzyl-[1,2,4]oxadiazol-3-yl)-4-hydroxy-benzoic acid;
4-Hydroxy-3-[5-(4-nitro-phenyl)-[1,2,4]oxadiazol-3-yl]-benzoic acid, and
4-Hydroxy-3-(5-isopropyl-[1,2,4]oxadiazol-3-yl)-benzoic acid.

2. A compound of the formula:

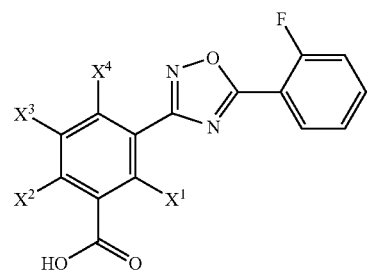

or a pharmaceutically acceptable salt thereof, wherein:
$X^1$, $X^2$, $X^3$ and $X^4$ are independently H or OH, and at least one of $X^1$, $X^2$, $X^3$ or $X^4$ is OH.

3. The compound of claim 2, wherein the compound is selected from the group consisting of:
3-[5-(2-fluorophenyl)-[1,2,4]oxadiazol-3-yl]-2-hydroxy-benzoic acid;
5-[5-(2-fluorophenyl)-[1,2,4]oxadiazol-3-yl]-2-hydroxy-benzoic acid; and
3-[5-(2-fluorophenyl)-[1,2,4]oxadiazol-3-yl]-5-hydroxy-benzoic acid.

4. A pharmaceutical composition comprising a compound of the formula:

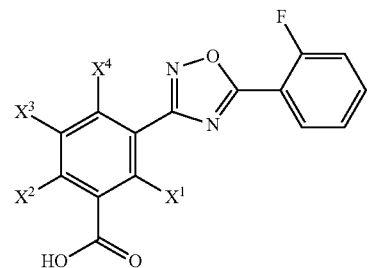

or a pharmaceutically acceptable salt thereof, wherein:
$X^1$, $X^2$, $X^3$ and $X^4$ are independently H or OH, and at least one of $X^1$, $X^2$, $X^3$ or $X^4$ is OH
and a pharmaceutically acceptable carrier, diluent or excipient.

5. The compound of claim 2, wherein said compound is a free acid.

6. The compound of claim 2, wherein said compound is a pharmaceutically acceptable salt.

7. The pharmaceutical composition of claim 4, wherein said compound is a free acid.

8. The pharmaceutical composition of claim 4, wherein said compound is a pharmaceutically acceptable salt.

* * * * *